(12) United States Patent
Braithwaite

(10) Patent No.: US 6,675,839 B1
(45) Date of Patent: Jan. 13, 2004

(54) FILLING METHOD

(75) Inventor: Phillip Braithwaite, Tewkesbury (GB)

(73) Assignee: Innovata BioMed Limited, St. Albans (GB)

( * ) Notice: Subject to any disclaimer, the term of this patent is extended or adjusted under 35 U.S.C. 154(b) by 0 days.

(21) Appl. No.: 09/582,866

(22) PCT Filed: Jan. 4, 1999

(86) PCT No.: PCT/GB99/00002
§ 371 (c)(1),
(2), (4) Date: Oct. 4, 2000

(87) PCT Pub. No.: WO99/34854
PCT Pub. Date: Jul. 15, 1999

(30) Foreign Application Priority Data

Jan. 3, 1998 (GB) ............................................. 9800020
Jan. 20, 1998 (GB) ............................................. 9801062

(51) Int. Cl.$^7$ ................................................ B65B 3/04
(52) U.S. Cl. .............................. 141/2; 141/18; 141/252; 141/319; 128/200.24
(58) Field of Search ............................... 141/2, 18, 113, 141/250, 252, 281, 284, 318, 319; 128/200.14, 203.19, 200.24

(56) References Cited

U.S. PATENT DOCUMENTS 1,858,735 A * 5/1932 Goodsell .................... 222/162
4,635,829 A * 1/1987 Brittingham, Jr. ........... 222/278
5,295,479 A 3/1994 Lankinen ................ 128/203.15

FOREIGN PATENT DOCUMENTS

| GB | 2235753 A | 3/1991 | ........... G01F/11/26 |
| WO | WO 93/16748 | 9/1993 | ........... A61M/15/00 |
| WO | WO 9912597 | 3/1999 | ........... A61M/15/00 |

OTHER PUBLICATIONS

International Search Report for PCT/GB99/00002, Apr. 28, 1999.

* cited by examiner

Primary Examiner—Timothy L. Maust
(74) Attorney, Agent, or Firm—Myers Bigel Sibley & Sajovec

(57) ABSTRACT

A method, and apparatus, for introducing a measured dose of powdered material into a dispensing device. The dispensing device includes two components which are relatively moveable between a first position, in which the two components together define a close space for accommodating the powdered material, and a second position in which the space is open separated from one of said components. The device is attached to a vessel partially filled with an amount of powdered material greater than that required to fill the space. The vessel is moved to a position at which the device lies below the level of the powdered material so that the powdered material occupies the space. The two components of the device are moved to their first position and the vessel is then moved to a position at which the attachment position lies above the powdered material and vessel. The device is then removed from the vessel.

8 Claims, 1 Drawing Sheet

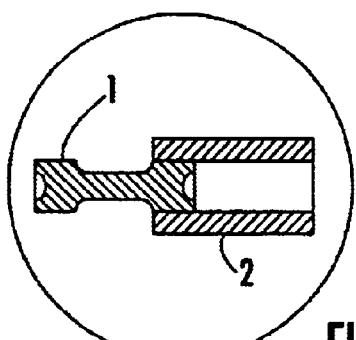
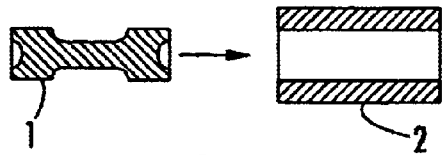
FIG. A
FIG. B
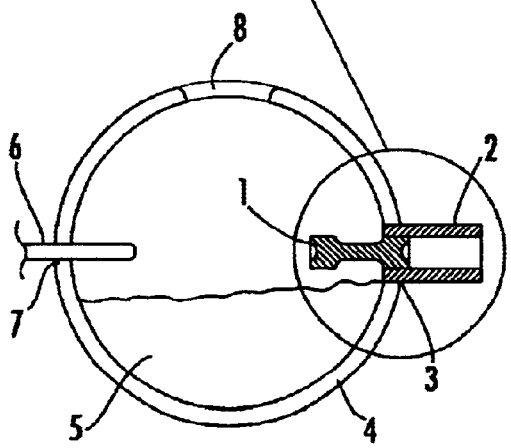
FIG. C
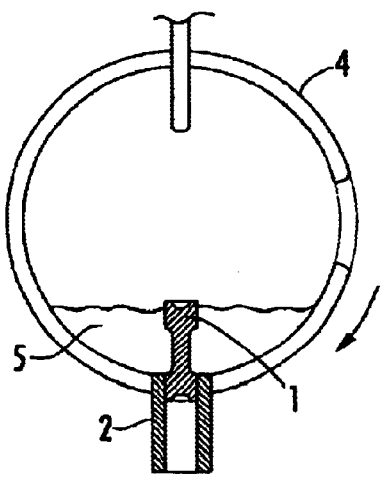
FIG. D
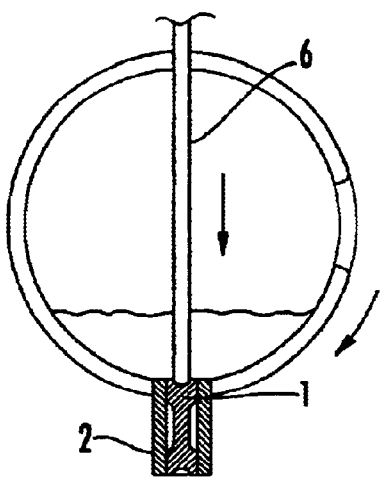
FIG. E
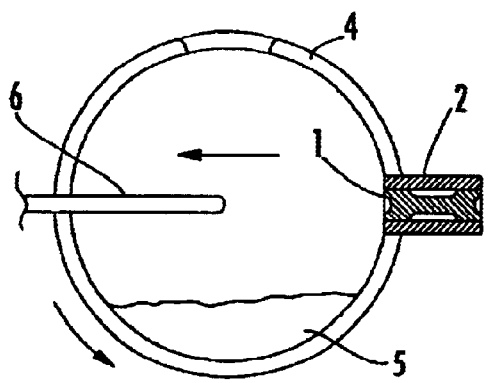
FIG. F

FILLING METHOD

FIELD OF THE INVENTION

This invention relates to methods and apparatus for introducing a measured or predetermined quantity of material into a dispensing device. The material may be any flowable material, including a powder or a liquid. One application of the present invention is in the field of medical inhalers in which a medicinal substance forms at least part of a micronized powder. The present invention enables an accurate dose of the powder to be introduced into the inhaler from which it may be inhaled by the patient. The medicinal substance may be for use in the treatment of diseases of the respiratory tract.

Reference will be made to the field of medical inhalers although it should be appreciated that the invention may have application in other fields, particularly those where small accurate doses of flowable material are required to be provided.

BACKGROUND OF THE INVENTION

A dry powder inhaler is disclosed in WO93/16748. Also disclosed in WO93/16748 is a metering device for use in transferring a desired volumetric dose of a flowable substance from a storage chamber containing the substance to a location outside the chamber. The metering device is suitable for use in the dry powder inhaler. The present invention provides an alternative dose providing device.

Another example of the application for the method and apparatus of the present invention is in connection with the aerosol producing device described in British Patent Application number 9719093.8 which describes a device for producing an aerosol, the device comprising a chamber having closure means operable to allow at least a partial vacuum to be created and maintained within the chamber, means for introducing substantially simultaneously into the chamber both a measurable quantity of powder and a gas so that an aerosol is formed within the chamber and exit means such that the aerosol may be withdrawn from the chamber.

It is an object of the present invention to provide a simple and effective means whereby an accurate dose of powder may be provided for introduction into a dispensing device. The dispensing device may be an inhaler, such as an inhaler of the type disclosed in the above mentioned earlier patent applications.

STATEMENTS OF INVENTION

According to the present invention there is provided a method of introducing a measured dose of powdered material into a dispensing device, said device including two components which are relatively moveable between a first position, in which the two components together define a closed space for accommodating said measured dose of powdered material, and a second position in which said space is open and separated from one of said components, the method comprising attaching the device to a vessel partially filled with an amount of said powdered material greater than that required to fill said space, said attachment being at a position above the level of the powdered material, moving said vessel to a position at which the device lies below the level of the powdered material, allowing said material to enter said space while the two components of the device are in their second position and said space is located within said vessel, relatively moving said two components of the device to their first position while retaining the powdered material in said space, moving said vessel to a position at which said attachment position lies above the powdered material in the vessel, and removing the device from said vessel.

The size of the measured dose retained within said device is determined by the extent of the free volume between the two components of the dispensing device. The extent of said free volume may, therefore, be varied in accordance with variations in the design of said components of said device.

Preferably, one of said two components of the device is in the form of a spool including enlarged end portions interconnected by an intermediate portion of reduced cross-section, and said other of the two components is a spool holder in the form of a tube or conduit within which the spool is slideable. A single dose of powder may then be sandwiched between the narrow part of the spool and the internal walls of the spool holder.

The spool and spool holder will hereinafter be referred to collectively as the spool assembly.

The design and dimensions of the spool assembly are such that the spool is able to move within the spool holder whilst maintaining sealing contact with the inner walls of the spool holder.

Partial displacement of the spool within the spool holder for the purposes of filling the assembly with a measured dose of powder may be achieved by sliding the spool to a point such that one of the enlarged end sections and the intermediate narrower portion having reduced cross-section are protruding beyond the end of the spool holder, the spool being held in place by the remaining enlarged end section, remaining within the spool holder.

Immersion of the spool within the powdered material may be achieved by attaching the spool assembly to a vessel or container holding said powdered material. Said vessel may comprise, for example a box, barrel or hopper but preferably is a cylindrical barrel including an orifice wherein the spool assembly may be inserted in order to provide an interface with the powdered material. Most conveniently, the dimensions of said orifice correspond with the external dimensions of the conduit, such that the assembly may be held in place whilst allowing the displaced section of the spool to protrude within the barrel.

In order to allow for ease of operation and convenience in use, the filling operation is preferably carried out using a cylindrical barrel which may be rotated about its central, longitudinal axis, the spool assembly is inserted into the orifice while the orifice is located above the level of the powdered material held within the barrel.

Subsequent rotation of the barrel brings the spool assembly to a position vertically below the longitudinal axis of the barrel at which position the spool is substantially immersed in the powdered material, at least to the extent of the narrower intermediate portion of the spool being wholly immersed in said powdered material.

Thereafter, by moving the spool into the spool holder, the powdered material will be carried into the spool assembly, filling the space defined by the narrower portion of the spool and the inner walls of the spool holder.

Insertion of the spool into the spool holder is most conveniently achieved by applying a force to the protruding end of the spool in order to push it into position within the conduit. Generally, a mechanical force may be applied, typically by means of a rod or pole, inserted through an orifice on the face of the barrel diametrically opposite the orifice to which the spool assembly is attached. The rod or pole may then be urged against the end of the spool to cause the spool to be pushed into the spool holder. Once the spool is fully housed within the spool holder, the rod or pole may be retracted.

Removal of the assembly containing the dose of powdered material from the barrel may be achieved by again rotating the barrel about its central axis to its original position above the level of powder within the barrel. The dosed assembly is then simply removed without disturbance or loss of the remaining powdered material held in the barrel.

The powdered material used in said dispensing device preferably includes a medicant, and said medicant is most preferably of the type used for the treatment of diseases of the respiratory tract.

The present invention also provides apparatus for introducing a measured dose of powdered material into a dispensing device, said device including two components which are relatively moveable between a first position in which the two components together define a closed space for accommodating said measured dose of powdered material, and a second position in which the said space is open and separated from one of said components, the apparatus comprising a vessel for accommodating a quantity of said powdered material less than an amount to fill the vessel but greater than the required to fill said space, means for attaching said device to said vessel so that, when the device is in its second position, said space is located within said vessel, means for moving said vessel, having the device attached thereto so as to raise or lower the space relative to the vessel, and means for effecting movement of the device, while attached to the vessel, from the second to the first position.

BRIEF DESCRIPTION OF THE DRAWINGS

The present invention will now be illustrated, though without limitation, by reference to the accompanying drawings, in which:

FIG. A shows a spool assembly conduit suitable for use in conjunction with the method of the present invention;

FIG. B shows the displaced arrangement of the spool assembly of FIG. A, ready for filling with the powdered material;

FIG. C shows the spool assembly of FIG. A held in the horizontal position in a cylindrical barrel prior to filling;

FIG. D shows the spool substantially immersed in the powdered material following rotation of the barrel through 90° about its central axis;

FIG. E shows the use of a rod to push the spool such that it becomes fully housed, together with the measured dose, within the spool holder, and FIG. F shows the dosed spool assembly again in the horizontal position and ready for removal following rotation of the barrel through 90° about its central axis.

DETAILED DESCRIPTION OF SPECIFIC EMBODIMENT

Referring firstly to FIG. A, the spool 1 is designed such that either enlarged end section may be inserted into, and provide a close fit within, the spool holder 2, thus providing the arrangement as shown in FIG. B. The resulting assembly may then be inserted into an orifice 3 in the side of a cylindrical barrel 4 which contains a bulk reservoir 5 of powdered medicant. Barrel 4 is equipped with a rod 6, inserted diametrically opposite the spool and conduit assembly, through an orifice 7 to give the arrangement shown in FIG. C. The barrel 4 also incorporates an openable lid 8 through which fresh medicant may be charged.

After attachment of the spool assembly, the barrel 4 is rotated clockwise through 90° such that the spool 1 is moved to the lower side of the barrel as seen in FIG. D, allowing the spool to become substantially immersed in the reservoir 5 of powdered medicant.

Referring to FIG. E, the use of the rod 6 to insert the spool 1 into the conduit 2 is illustrated. Thus, by depression of the rod, a force is applied to the spool such that the spool is pushed into the conduit, carrying with it a sample of the medicant powder sufficient to fill the space between the narrower middle section of the spool and the internal walls of the spool holder, and thereby providing a single, measured dose of medicant.

It can then be seen from FIG. F that rotation of the barrel 4 anti-clockwise through 90° returns the spool assembly to its original position relative to the reservoir 5 of powdered medicant. Following retraction of the rod 6, it is then possible to remove the spool assembly, containing the dose of medicant, from the barrel, allowing for administration of the dose to a patient by means of a suitable inhaler, such as that disclosed in co-pending British Patent Application No. 9719093.8 or in WO93/16748.

In another embodiment, the vessel is substantially barrel shaped but it includes a lobe or ear portion into which the spool may project and into which the powder may collect for the filling of the space associated with the spool.

What is claimed is:

1. A method of introducing a measured dose of powdered material into a dispensing device, said device including two components which are relatively moveable between a first position, in which the two components together define a closed space for accommodating said measured dose of powdered material, and a second position in which said space is open and separated from one of said components, the method comprising attaching the device to a vessel partially filled with an amount of said powdered material greater than that required to fill said space, said attachment being at a position above the level of the powdered material, moving said vessel to a position at which the device lies below the level of the powdered material, allowing said material to enter said space while the two components of the device are in their second position and said space is located within said vessel, relatively moving said two components of the device to their first position while retaining the powdered material in said space, moving said vessel to a position at which said attachment position lies above the powdered material in the vessel, and removing the device from said vessel.

2. A method according to claim 1 wherein the two components of the device are in their second position prior to movement of the vessel to the position at which the device lies below the level of the powdered material.

3. A method according to claim 1 wherein one of said two components of the device is in the form of a spool and the other of said two components is a spool holder in the form of a tube or conduit within which the spool is slideable.

4. A method according to claim 1 wherein the vessel is in the form of a substantially cylindrical barrel.

5. A method according to claim 1 wherein the vessel is in the form of a substantially cylindrical barrel and includes a lobe or ear portion to which the device may be attached and into which the powder may collect for the filling of the space.

6. A method according to claim 1 wherein the powdered material includes a medicament.

7. A method according to claim 6 wherein the medicament is for the treatment of a disease of the respiratory tract.

8. Apparatus for introducing a measured dose of powdered material into a dispensing device, said device including two components which are relatively moveable between a first position in which the two components together define a closed space for accommodating said measured dose of powdered material, and a second position in which the said space is open and separated from one of said components, the apparatus comprising a vessel for accommodating a quantity of said powdered material less than an amount to fill the vessel but greater than that required to fill said space, means for attaching said device to said vessel so that, when the device is in its second position, said space is located within said vessel, means for moving said vessel, having the device attached thereto, so as to raise or lower the space relative to the vessel, and means for effecting movement of the device, while attached to the vessel, from the second to the first position.

* * * * *